US008783003B2

(12) United States Patent
Czajka, Jr. et al.

(10) Patent No.: US 8,783,003 B2
(45) Date of Patent: Jul. 22, 2014

(54) METHOD PERTAINING TO A MULTI-COLORED STERILIZATION WRAP

(75) Inventors: Francis A. Czajka, Jr., Libertyville, IL (US); Dixit Gandhi, Chicago, IL (US); Alan E. Weiss, Highland Park, IL (US)

(73) Assignee: Medline Industries, Inc., Mundelein, IL (US)

( * ) Notice: Subject to any disclaimer, the term of this patent is extended or adjusted under 35 U.S.C. 154(b) by 125 days.

(21) Appl. No.: 13/418,701

(22) Filed: Mar. 13, 2012

(65) Prior Publication Data
US 2013/0240399 A1  Sep. 19, 2013

(51) Int. Cl.
*A61B 19/02* (2006.01)
*A61L 2/26* (2006.01)
*B65B 63/04* (2006.01)
*B65B 35/56* (2006.01)
*B65B 35/50* (2006.01)
*B65B 25/14* (2006.01)
*B32B 7/02* (2006.01)

(52) U.S. Cl.
CPC ............... *B65B 63/04* (2013.01); *B65B 35/56* (2013.01); *B65B 35/50* (2013.01); *B65B 25/141* (2013.01); *B65B 25/145* (2013.01); *B65B 25/146* (2013.01); *A61B 19/026* (2013.01); *A61L 2/26* (2013.01); *B32B 7/02* (2013.01); *Y10S 116/41* (2013.01)
USPC ............. 53/430; 53/429; 53/475; 206/459.1; 116/DIG. 41

(58) Field of Classification Search
CPC .......... B32B 7/02; B65B 63/04; B65B 35/56; B65B 35/50; B65B 25/146; B65B 25/143; B65B 25/141; B65B 25/14; B65B 5/10; B65B 5/06; A61B 19/026; A61B 19/02; A61B 2019/4847; A61B 2019/4836; A61L 2/26; Y10S 116/41

USPC ............ 53/430, 447, 473, 475; 116/200, 201, 116/DIG. 41; 206/438, 439, 459.1; 422/1, 422/292; 428/195.1
IPC ............. B65B 63/04,35/56, 35/50, 25/14, 5/10, B65B 5/06; A61B 19/02; A61L 2/26
See application file for complete search history.

(56) References Cited

U.S. PATENT DOCUMENTS 5,635,134 A * 6/1997 Bourne et al. ................. 422/26
5,688,476 A   11/1997 Bourne et al.
(Continued)

FOREIGN PATENT DOCUMENTS

WO   WO 2008/083426       7/2008
WO   WO 2009143551 A1 * 12/2009 ................ A61L 2/26

OTHER PUBLICATIONS

Kimberly-Clark Health Care Introduces KIMGUARD* Sterilization Wrap for Confident Inspection; Roswell, GA and New Orleans, Mar. 26, 2012/PRNewswire; http://www.kchealthcare.com, 2 pages.

(Continued)

*Primary Examiner* — Stephen F Gerrity
(74) *Attorney, Agent, or Firm* — Fitch Even Tabin & Flannery LLP (57) ABSTRACT

Sterilization wraps have a first side colored at least a first color and an opposing second side colored at least a second color that is different than the first color. These sterilization wraps are then paired such that each of the pairs of sterilization wraps has the aforementioned first sides of the sterilization wraps that comprise the pair of sterilization wraps facing one another. By one approach these pairs of sterilization wraps are un-bonded and hence are not physically connected to one another. By another approach the sterilization wraps that comprise a given pair can be coupled to one another (for example, by an intermingling of the materials that comprise the two sterilization wraps). A plurality of such pairs of sterilization wraps can then be placed in a suitable container to facilitate handling, storage, and shipment.

16 Claims, 5 Drawing Sheets

(56) References Cited

U.S. PATENT DOCUMENTS

| | | |
|---|---|---|
| 2002/0124947 A1 | 9/2002 | Kim |
| 2003/0196921 A1* | 10/2003 | Giordano ............... 206/459.1 |
| 2004/0261373 A1 | 12/2004 | Bowen et al. |
| 2005/0079093 A1 | 4/2005 | Cannady et al. |
| 2005/0163654 A1* | 7/2005 | Stecklein et al. ............ 422/294 |
| 2005/0170726 A1* | 8/2005 | Brunson et al. ............. 428/212 |
| 2006/0067855 A1 | 3/2006 | Mathis et al. |
| 2006/0104856 A1 | 5/2006 | Farrell et al. |
| 2006/0104857 A1 | 5/2006 | Pigott et al. |
| 2007/0224409 A1* | 9/2007 | Dovorany et al. ........ 428/304.4 |
| 2008/0083426 A1 | 4/2008 | Sachdev et al. |
| 2011/0033137 A1 | 2/2011 | Gaynor et al. |
| 2013/0171427 A1* | 7/2013 | Pamperin et al. ............ 428/192 |

OTHER PUBLICATIONS

International Search Report and Written Opinion Dated Jun. 21, 2013 from PCT/US2013/029373, 9 pages.

* cited by examiner

METHOD PERTAINING TO A MULTI-COLORED STERILIZATION WRAP

TECHNICAL FIELD

This invention relates generally to sterilization wraps.

BACKGROUND

Sterilization wraps are known in the art. Sterilization wraps typically comprise a sheet of material that a user wraps around one or more items (such as, for example, surgical instruments) that are to be heated (for example, in an autoclave) in order to sterilize those items. The sterilized, wrapped item(s) can then be removed from the heating/sterilization appliance and stored, while still wrapped, for future use. At a time of need the user removes the wrapping to permit access to the still-sterile items.

Sterilization wraps sometimes comprise a cloth or crepe paper material. Many times, however, the sterilization wrap comprises a polypropylene-based material. Industry standards recommend the use of a very thick single sheet (an uncommon approach in practice) or the use of two sheets wrapped sequentially or simultaneously. This two-ply approach often comprises using a pair of identical sterilization wraps that are bonded to one another in order to ensure the use of both plies in a single step. This bonding can comprise, for example, ultrasonic welding along (or near) the periphery of a juxtaposed pair of sterilization wraps of the same size.

The practice of bonding two sterilization wraps to create an integral two-ply sterilization wrap, of course, adds effort, cycle time, and cost to the manufacturing process. Some practitioners may express concern, however, that they might inadvertently use only a single sheet when wrapping an item to be sterilized unless the two sheets are bonded to one another.

Small punctures, such as pin pricks or needle pricks, are another potential cause for concern when using sterilization wraps. Such small apertures in the wrapping material are typically very small and hence hard to observe. Unfortunately, though small, these openings may be sufficient to permit dust, bacteria, and other contaminants access to the items that are wrapped within a sterilization wrap.

BRIEF DESCRIPTION OF THE DRAWINGS

The above needs are at least partially met through provision of the method and apparatus pertaining to a multi-colored sterilization wrap described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, sterilization wraps have a first side colored at least a first color and an opposing second side colored at least a second color that is different than the first color. These sterilization wraps are then paired such that each of the pairs of sterilization wraps has the aforementioned first sides of the sterilization wraps that comprise the pair of sterilization wraps facing one another. So configured, each pair of sterilization wraps presents the second color on its outwardly-facing sides while the first colored sides face inwardly towards one another.

By one approach these pairs of sterilization wraps are un-bonded and hence are not physically connected to one another. By another approach, if desired, the sterilization wraps that comprise a given pair can be coupled to one another (for example, by an intermingling of the materials that comprise the two sterilization wraps).

A plurality of such pairs of sterilization wraps can then be placed in a suitable container to facilitate handling, storage, shipment, and use. By one approach this can comprise simply stacking these pairs of sterilization wraps in the container one atop another. If desired, the sterilization sheets as comprise a given pair can be offset in some manner from one another in order to visually expose both the aforementioned first side of one sterilization wrap and the aforementioned second side of the other sterilization wrap. Using this approach an observer can readily observe both the first color and the second color. This, in turn, can help to facilitate ensuring that a medical-services provider uses two sterilization wraps when wrapping items for sterilization and not merely one sterilization wrap by mistake.

These teachings are highly flexible in practice and will accommodate great variety with respect to the colors (and patterns), materials, shapes, and material weights employed. These teachings will also readily accommodate a wide variety of packaging approaches. For example, the approaches described herein will accommodate stacking adjacent pairs of sterilization wraps in a manner that permits two wraps at a time to be reliably grasped and withdrawn from the container. As another example these approaches will readily accommodate providing the pairs of sterilization wraps in a roll-based form factor.

So configured, reliable and effective use of two sterilization wraps can be prompted and effected without necessarily requiring any physical connection between those two wraps. This, in turn, can lead to reduced costs while also offering some increased flexibility regarding the manner of use of such wraps in a given application setting. In addition, the use of differing colors as described can improve the ability of the observe to spot small apertures such as pin pricks and needle pricks in the sterilization wrap material. This ability to spot small holes, in turn, can lead to increased safety for patients.

These and other benefits may become clearer upon making a thorough review and study of the following detailed description. Prior to providing that detailed description, however, it may be useful to first provide a few more details regarding the use of sterilization wraps.

Figure 1:
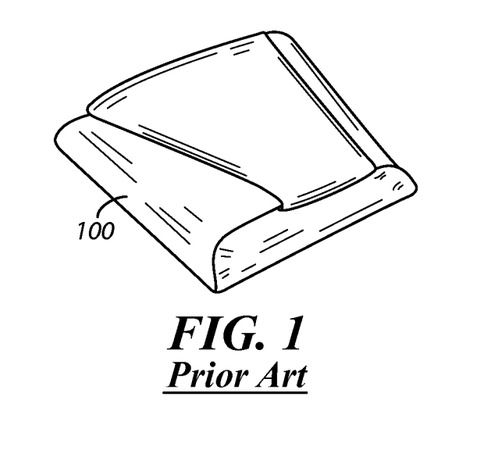
FIG. 1 comprises a perspective view as configured in accordance with the prior art.

As shown in FIG. 1, sterilization wraps (such as a pair of sterilization wraps) 100 are typically wrapped around items to be sterilized. The wrapping process typically involves a precise and somewhat convoluted folding process in order to present no better than a tortuous and circuitous pathway for airborne contaminants to thereby aid in maintaining the sterility of the items during storage. In many cases one or more strips of tape (not shown) will be applied to the wrapped package to help to maintain the wrapped state of the package.

Figure 2:
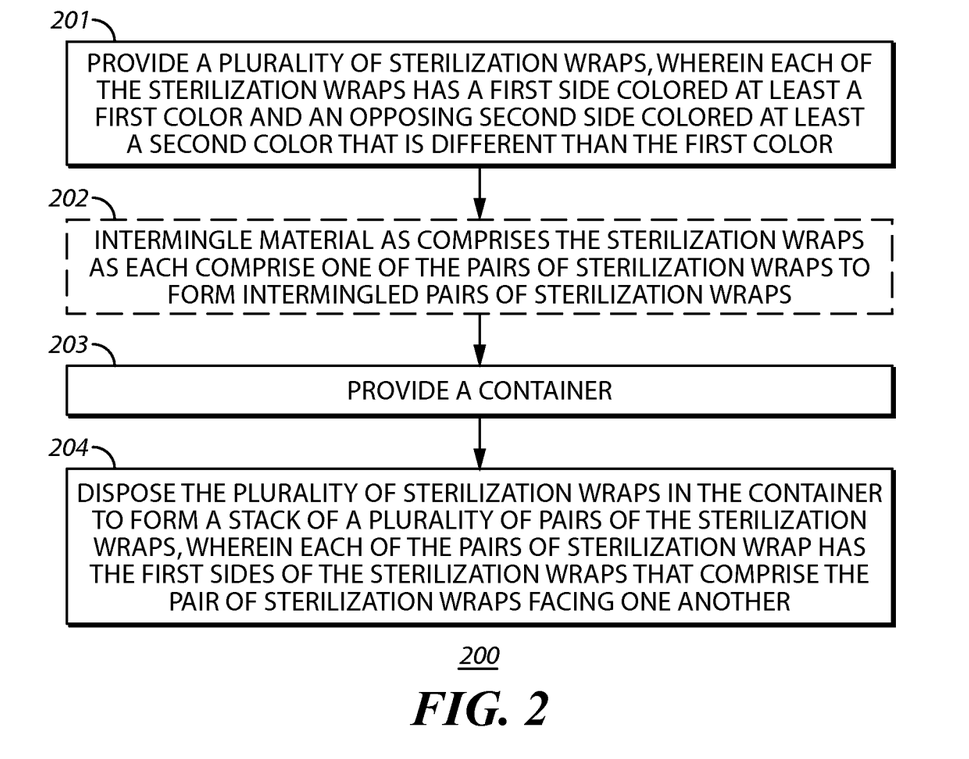
FIG. 2 comprises a flow diagram as configured in accordance with various embodiments of the invention.
Figure 3:
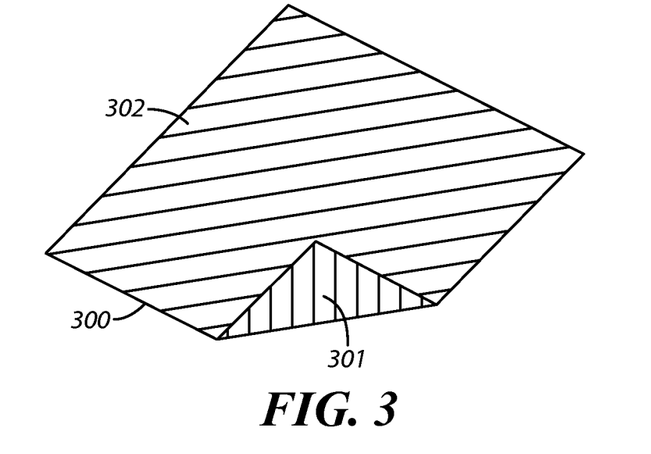
FIG. 3 comprises a perspective view as configured in accordance with various embodiments of the invention.

Referring now to FIG. 2, a process 200 that illustrates at least some aspects in accordance with the present teachings will be described. This process 200 includes the step 201 of providing a plurality of sterilization wraps. As shown in FIG. 3, each of these sterilization wraps 300 has a first side colored at least a first color 301 (symbolically represented here as a pinkish color) and an opposing second side colored at least a second, different color 302 (symbolically represented here as a bluish color).

By one approach, each side of the sterilization wrap 300 completely comprises a solid color. These teachings will accommodate other approaches in these regards, however. This can include any of a variety of multi-hued or multi-colored patterns. Generally speaking, for many application settings it will serve well if the first color comprises a contrasting color as compared to the second color (such as, for example, a lighter, brighter color as compared to a darker color). The use of contrasting colors can help to facilitate an observer noticing small holes that are disposed through the sterilization wrap 300.

Generally speaking, such a sterilization wrap 300 often has a rectangular form factor including, as shown in FIG. 3, a square form factor. Such an approach accords well with established practices regarding the use of such a wrap to package items to be sterilized and stored in a sterilized state. That said, the present teachings will accommodate other form factors, such as but not limited to triangular form factors or oval-shaped form factors, if desired.

The present teachings can also be applied in conjunction with a variety of materials. By one approach, for example, the sterilization wrap 300 comprises a spunbound and/or melt-blown material as is known in the art. These teachings will also accommodate materials having any of a variety of weights (often expressed by use of the metric "grams per square meter") such as, for example, materials ranging from thirty-five to eighty-five grams per square meter. If desired, at least one of the aforementioned colors can have a color or a color-based property (such as hue) that correlates to the weight of the material that comprises the sterilization wrap 300. Such a practice can assist the user with respect to selecting a particular desired weight of sterilization wrap by simply noting the color or color-based properties of the available sterilization wraps.

As will be described momentarily in more detail, this process 100 provides for arranging these sterilization wraps 300 in a particular way as pairs of sterilization wraps. For many application settings it will suffice for such pairs to comprise pairs of sterilization wraps 300 that are not physically bound to one another. This process 100 will accommodate physically coupling the constituent sterilization wraps 300 of such pairs if desired, however.

Figure 4:
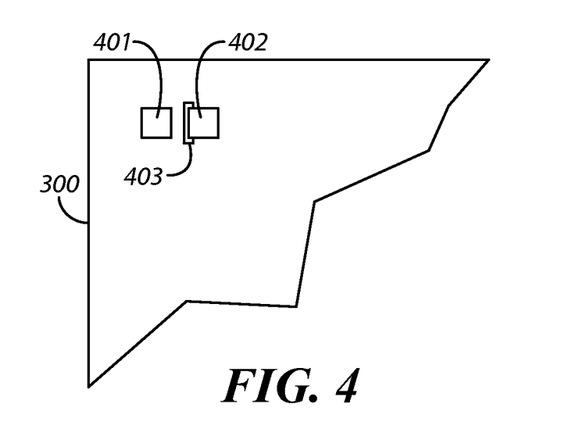
FIG. 4 comprises a top plan detail view as configured in accordance with various embodiments of the invention.

By one approach this coupling can comprise binding two sterilization wraps 300 to one another with ultrasonic welding, thread, brads, staples, or the like. With reference to FIGS. 2 and 4, this can also comprise, as yet another example, the optional step 202 of intermingling material as comprises the sterilization wraps 300 to thereby form intermingled pairs of sterilization wraps 300. As one illustrative example in these regards, a tab 402 of material from back-to-back sterilization wraps 300 can be formed and disposed through a slot 403 formed through the sterilization wraps 300 (leaving a hole 401 formed by the tab material). Such a coupling mechanism can be applied, for example, proximal each of the corners of the sterilization wraps 300. These teachings will accommodate other ways of intermingling the material that comprises the sterilization wraps 300 of a pair of such wraps 300 as desired.

Figure 5:
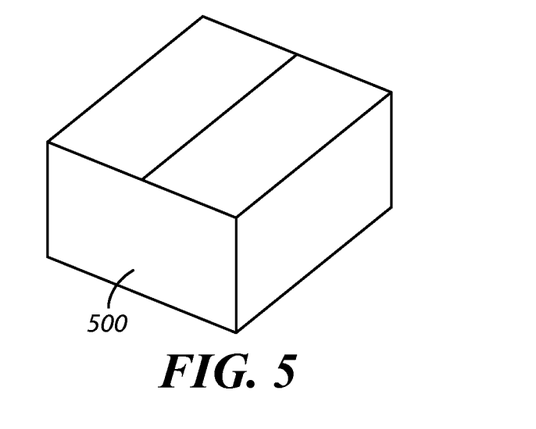
FIG. 5 comprises a perspective view as configured in accordance with various embodiments of the invention.

Referring to FIGS. 2 and 5, this process 200 in any event includes the step 203 of providing a container 500. This container 500 can comprise, for example, a box comprised of paperstock material (such as corrugated or non-corrugated cardboard). The container 500 can be comprised of essentially any material that may suffice to meet the needs of a given application setting and can have essentially any shape and/or relative rigidity or flexibility. So configured, such a container will accommodate a plurality of the sterilization wraps 300 to facilitate storing, distributing, and dispensing those sterilization wraps 300 as desired.

Figure 6:
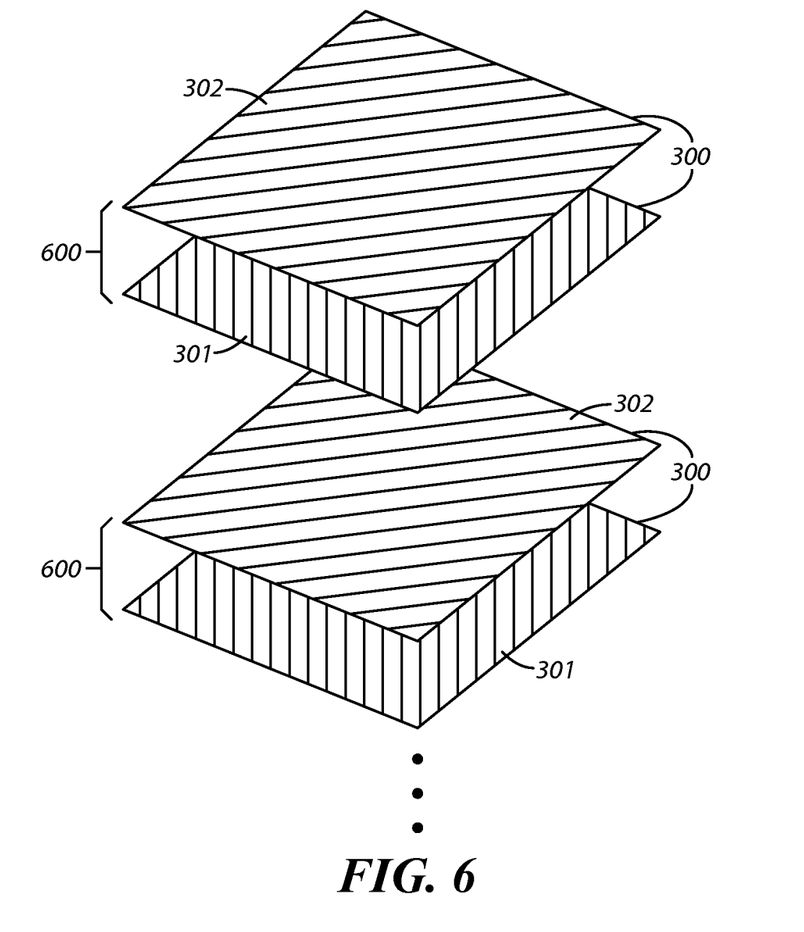
FIG. 6 comprises a perspective exploded view as configured in accordance with various embodiments of the invention.
Figure 7:
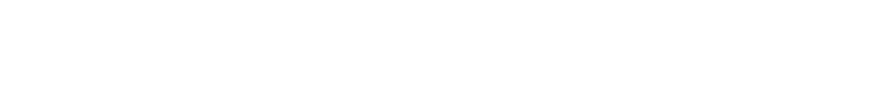
FIG. 7 comprises a side elevational view as configured in accordance with various embodiments of the invention.

Referring to FIGS. 2, 6, and 7, this process 200 then provides the step 204 of disposing the plurality of sterilization wraps 300 in the container 500 to form a stack 700 of a plurality of pairs 600 of the sterilization wraps 300, where each of the pairs 600 of sterilization warps has the first sides (and hence the first color 301) of the sterilization wraps 300 that comprise a given pair 600 of sterilization wraps 300 facing one another. Such a stack 700 might comprise, for example, from about twenty-five such pairs 600 to five hundred or more such pairs 600 as desired.

Accordingly, a given pair 600 of sterilization wraps 300 presents the second color 302 (which might comprise, for example, a bluish color) on both of the outwardly-facing surfaces of the pair 600 of sterilization wraps 300. Similarly, the first color 301 (which might comprise a different, contrasting color, such as a pinkish color) for both of the sterilization wraps 300 that comprise a given pair 600 will face inwardly of the pair 600.

A number of advantages correspond to such an arrangement. For example, should the user grasp only one of the sterilization wraps 300 rather than two, this likely mistake will be immediately visually evident as the first color (i.e., the inwardly directed and hence ordinarily hidden color) will be immediately and obviously visible on the top of the stack 700. The user can readily take note of this circumstance and correct their action by also taking that next sterilization wrap 300. Accordingly, such an approach will tend to help ensure that two sterilization wraps 300 are used when wrapping an item to be sterilized notwithstanding that the wraps 300 are not physically bonded to one another.

As another example, and presuming in particular the use of contrasting colors for the first and second colors 301 and 302, in many application settings it can be easier to detect, by the use of only ordinary vision, when a small opening through the sterilization wrap 300 material exists for a wrapped item. This, in turn, can help to ensure that previously-sterilized items for which the sterilization may be compromised are not used until they are re-sterilized.

In the examples suggested above, the pairs 600 of sterilization wraps 300 are stacked with the wraps 300 being essentially coextensive with one another. These teachings will accommodate other practices in these regards, however. It may be useful in some application settings, for example, to arrange the sterilization wraps 300 that comprise a given pair 600 in an offset manner. Such a configuration can permit at least a bit of the first color 301 to be visible to thereby further facilitate the user correctly selecting a pair of the sterilization wraps 300 and not merely one sterilization wrap 300.

Figure 8:
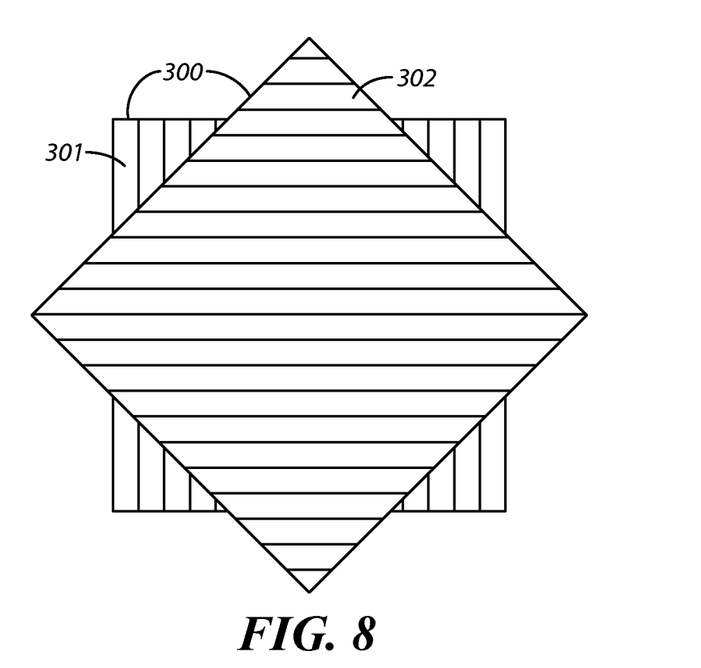
FIG. 8 comprises a top plan view as configured in accordance with various embodiments of the invention.

FIG. 8 provides one illustrative example in these regards where one of the sterilization wraps 300 for each pair 600 is oriented at a forty-five degree angle to the remaining sterilization wrap 300 for each pair 600. Other offsetting approaches are of course possible. To achieve something of a similar result, it would also be possible to cut a corner from (or to form an opening through) every other sterilization wrap 300 to similarly expose the first color 301 to ordinary view.

Figure 9:
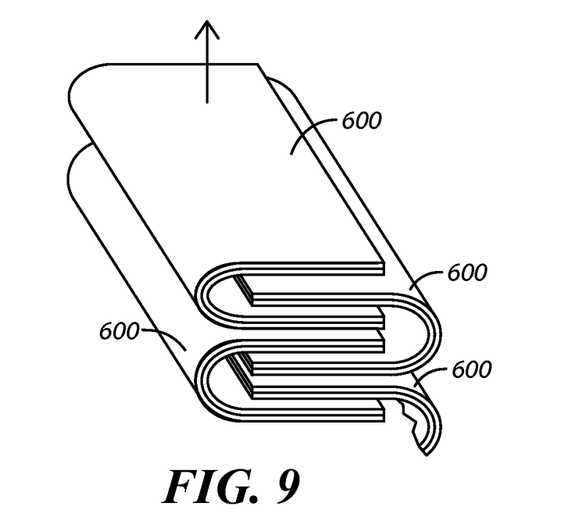
FIG. 9 comprises a perspective view as configured in accordance with various embodiments of the invention.

The present teachings are highly flexible in practice and will in fact accommodate a wide range of packaging approaches. As one illustrative example in these regards, and referring to FIG. 9, a cross-folding approach can be used to permit individual pairs 600 of sterilization wraps 300 to be rendered individually dispensible in a manner akin to removing facial tissues one at a time from a box of such tissues.

Figure 10:
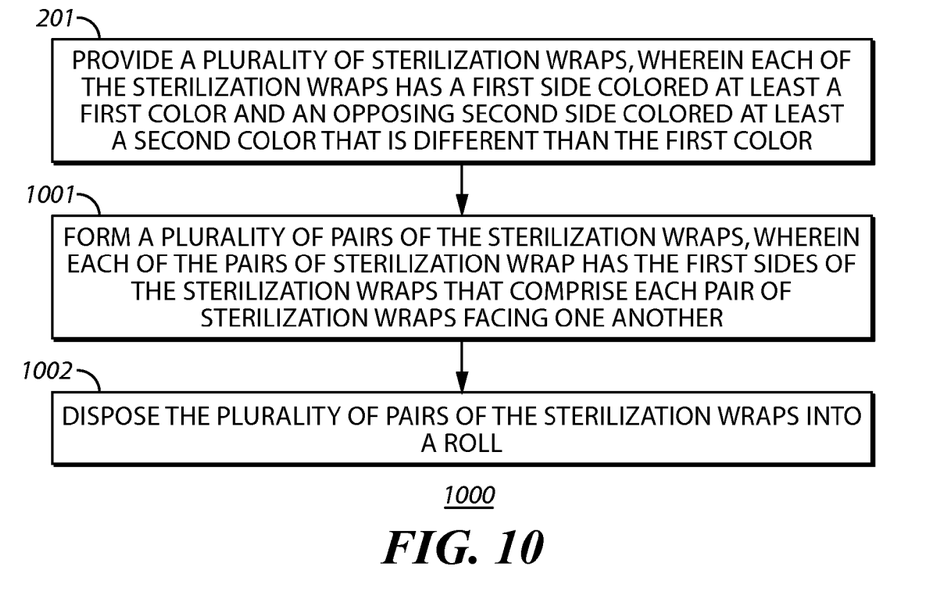
FIG. 10 comprises a flow diagram as configured in accordance with various embodiments of the invention.

As a further illustration of the flexibility of these teachings, FIG. 10 illustrates a process 1000 that again includes the step 201 of providing the aforementioned sterilization wraps 300 and which then provides the step 1001 of forming a plurality of pairs 600 of the sterilization wraps 300 (having the same color-based orientation as before) and the step 1002 of disposing that plurality of pairs 600 of sterilization wraps 300 into a roll.

Figure 11:
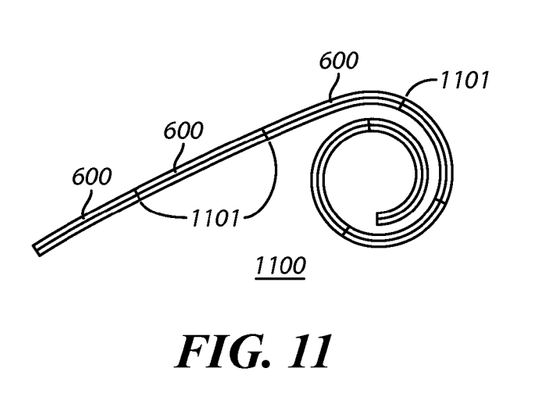
FIG. 11 comprises a side elevational view in accordance with various embodiments of the invention.

FIG. 11 depicts one such approach, where the resultant roll 1100 comprises pairs 600 of sterilization wraps 300 that are connected as a series of pairs 600 of sterilization wraps 300. Perforations or scoring 1101 can serve as a means of defining each pair 600 and as a convenient way for the user to separate a single pair 600 of sterilization wraps 300 from the roll 1100.

Figure 12:
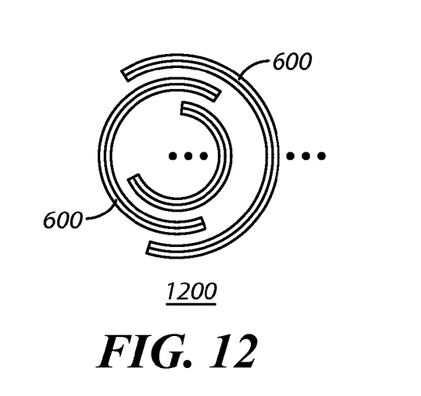
FIG. 12 comprises a side elevational view in accordance with various embodiments of the invention.

FIG. 12 depicts another approach in such regards. In this example the resultant roll 1200 simply comprises a roll of individually-segregated pairs 600 of sterilization wraps 300 that can be selected and individually removed as needed.

These teachings permit sterilization wraps to be used in an ordinary manner and pursuant to ordinary standards and requirements without requiring the employment of expensive bonding techniques. These teachings will also facilitate noting small openings that may form in the material to thereby help avoid the use of sterilized items for which the sterility is compromised. The described concepts are readily employed with sterilization wraps having any of a variety of sizes, shapes, and weights.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
providing a plurality of sterilization wraps, wherein each of the sterilization wraps has a first side colored at least a first color and an opposing second side colored at least a second color that is different than the first color;
providing a container;
intermingling material as comprises the sterilization wraps as each comprise one of the pairs of sterilization wraps to form intermingled pairs of sterilization wraps;
disposing the intermingled pairs of sterilization wraps in the container to form a stack of a plurality of intermingled pairs of the sterilization wraps, wherein each of the pairs of sterilization wraps has the first sides of the sterilization wraps that comprise the pair of sterilization wraps facing one another.

2. The method of claim 1 wherein each of the sterilization wraps has a rectangular form factor.

3. The method of claim 2 wherein the rectangular form factor comprises a square form factor.

4. The method of claim 1 wherein the first color comprises a bluish color.

5. The method of claim 4 wherein the second color comprises a pinkish color.

6. The method of claim 1 wherein each of the sterilization wraps as comprises one of the intermingled pairs of the sterilization wraps have at least substantially-identical grams-per-square-meter ratings.

7. The method of claim 6 wherein the second color identifies, at least in part, the grams-per-square-meter rating of the sterilization wraps.

8. The method of claim 1 wherein the first side is completely colored the first color.

9. The method of claim 8 wherein the second side is completely colored the second color.

10. The method of claim 1 wherein the first color comprises a contrasting color as compared to the second color to thereby facilitate noticing small holes disposed through the sterilization wrap.

11. The method of claim 1 wherein disposing the intermingled pairs of sterilization wraps in the container to form a stack of a plurality of intermingled pairs of the sterilization wraps comprises stacking the plurality of intermingled pairs of the sterilization wraps in a cross-folded manner.

12. A method comprising:
providing a plurality of sterilization wraps, wherein each of the sterilization wraps has a first side colored at least a first color and an opposing second side colored at least a second color that is different than the first color;
forming a plurality of pairs of the sterilization wraps, wherein each of the pairs of sterilization wraps has the first sides of the sterilization wraps that comprise each pair of sterilization wraps facing one another;
disposing the plurality of pairs of the sterilization wraps into a roll.

13. The method of claim 12 wherein the first side is completely colored the first color.

14. The method of claim 13 wherein the second side is completely colored the second color.

15. The method of claim 12 wherein the first color comprises a contrasting color as compared to the second color to thereby facilitate noticing small holes disposed through the sterilization wrap.

16. The method of claim 12 wherein disposing the plurality of pairs of the sterilization wraps into a roll comprises disposing the plurality of pairs of the sterilization wraps as a roll of pairs of the sterilization wraps that are connected as a series of pairs of the sterilization wraps.

\* \* \* \* \*